(12) United States Patent
Heffelfinger et al.

(10) Patent No.: US 9,655,700 B2
(45) Date of Patent: May 23, 2017

(54) METHOD OF MAKING A DENTURE WITH NATURAL BITE AND WEAR PROPERTIES AND DENTURE

(71) Applicant: Bite Innovations, LLC, Auburn, IN (US)

(72) Inventors: Nathaniel Heffelfinger, Auburn, IN (US); Larry Stoller, Bluffton, IN (US)

( * ) Notice: Subject to any disclaimer, the term of this patent is extended or adjusted under 35 U.S.C. 154(b) by 21 days.

(21) Appl. No.: 14/743,107

(22) Filed: Jun. 18, 2015

(65) Prior Publication Data

US 2016/0367344 A1 Dec. 22, 2016

(51) Int. Cl.
*A61C 13/097* (2006.01)
*A61C 13/00* (2006.01)

(52) U.S. Cl.
CPC ........ *A61C 13/097* (2013.01); *A61C 13/0004* (2013.01); *A61C 13/0024* (2013.01)

(58) Field of Classification Search
CPC .............. A61C 13/097; A61C 13/0004; A61C 13/0024
See application file for complete search history.

(56) References Cited

U.S. PATENT DOCUMENTS

| | | | |
|---|---|---|---|
| 4,302,187 A | 11/1981 | Yoon | |
| 4,642,052 A | 2/1987 | Carlson | |
| 5,678,993 A | 10/1997 | Jeffer et al. | |
| 6,056,546 A | 5/2000 | Van Handel | |
| 7,153,135 B1 | 12/2006 | Thomas | |
| 2005/0112523 A1 | 5/2005 | Massad | |
| 2006/0093987 A1* | 5/2006 | Wen ..................... | A61C 9/002 433/74 |
| 2006/0099552 A1* | 5/2006 | van der Zel ............. | A61C 5/10 433/223 |
| 2009/0104585 A1* | 4/2009 | Diangelo ............. | A61C 8/0001 433/223 |
| 2012/0322031 A1 | 12/2012 | Kim | |
| 2013/0101962 A1 | 4/2013 | Howe | |
| 2013/0316302 A1 | 11/2013 | Fisker | |
| 2015/0182316 A1* | 7/2015 | Morales ................. | A61C 13/01 433/199.1 |

FOREIGN PATENT DOCUMENTS

CN 102178564 A 9/2011
CN 103770223 A 5/2014

OTHER PUBLICATIONS

Joanne M. Livaditis et. al., The Use of Custom-Milled Zirconia Teeth to Address Tooth Abrasion in Complete Dentures; A Clinical Report, 22 Journal of Prosthodontics 208-213, published 2013, passim.

* cited by examiner

*Primary Examiner* — Eduardo C Robert
*Assistant Examiner* — Julianna N Harvey (57) ABSTRACT

The present invention is directed to a method of denture manufacture that incorporates CAM-formed occlusal inserts made of zirconia, resulting in a natural lit, feel, and wear essentially equivalent to the wear properties of natural teeth.

20 Claims, 5 Drawing Sheets

METHOD OF MAKING A DENTURE WITH NATURAL BITE AND WEAR PROPERTIES AND DENTURE

CROSS-REFERENCES TO RELATED APPLICATIONS

Not Applicable

STATEMENT REGARDING FEDERALLY SPONSORED RESEARCH OR DEVELOPMENT

Not applicable

BACKGROUND

This invention relates a method of making an artificial full or partial denture with natural bite and wear properties.

Full and partial artificial dentures are well known to the art. A full or partial denture is defined herein as a removable implantable structure overfitting all or part of the upper gums with some or all teeth removed, or all or part of the lower gums with some or all teeth removed, and providing occlusal surfaces that can be used for chewing in lieu of natural teeth.

It is a longstanding goal of dentists and other professionals involved in denture manufacture to create dentures that, when worn, feel and fit as similar as possible to the patient's natural teeth. To obtain this feel and fit, defined herein as "natural," it is necessary to create dentures that, when used, result in a resting jaw position, bite pattern, occlusal contact, and relative tooth movement as similar as possible to that of the patient's natural teeth. This will be referred to herein as the patient's "natural bite." For dentures to maintain a natural bite feel, it is further necessary for artificial teeth within the denture to wear at a rate similar to the wear rate of natural teeth.

The first step in one common method of denture manufacture involves assessment by the dentist of the patient's natural bite or desired bite. Such assessment is typically conducted by measuring the patient's jaw and collecting preliminary impressions of landmark structures in the patient's mouth. These preliminary impressions are used to create a custom impression tray. A denturist or other skilled artisan often makes the custom impression tray. The patient is then fitted with the custom impression tray for more detailed functional impressions of the patient's oral structures, and for assessment of the patient's muscle movements during speech and mastication. The dentist next performs occlusal registration, commonly using wax bite registration, tactile bite registration, intra-oral pin tracing, or gnathometer bite registration techniques. Next, the dentist selects artificial teeth of desired size and shape for attachment to that base. The size and shape of the artificial teeth is selected to most closely replicate the patient's natural or desired bite, as determined by the measurements data collected during the assessment.

The selected artificial teeth are then set in wax try-in base for a test fitting with the patient. Alternatively, the artificial teeth may be removably inserted into a base, such as an acrylic base, intended as the permanent base. The patient provides feedback on the fit and feel of the denture, and the dentist makes any necessary adjustments to the parameters of the base, as well, or optionally alternatively to, the size, shape, and placement of the artificial teeth. Once the patient is satisfied with the look, fit, and feel of the try-in denture, a permanent denture of substantially similar configuration is made by attaching the artificial teeth to a permanent base.

As can be seen, manufacturing dentures to achieve a natural bite feel for the patient is a time and labor intensive process. The manufacture of dentures generally involves an iterative process of test-fitting and reshaping, and involve the time of both a dentist and the time of a skilled denturist or other artisan. A patient may require three, four, five, or even more test-fittings before the denture is satisfactorily shaped and sized.

It is known to the art to increase the precision of the denture manufacture process through the use of computer-aided drawing (CAD) software, often linked to milling, cutting, or other shaping machines capable of forming material in accordance with instructions delivered by CAD software. Such machines will be referred to herein as computer-aided manufacture (CAM) machines. For example, it is known to the art to use a haptic device to allow a computer to create a three-dimensional digital CAD model of a denture based on the patient's oral structures. An actual denture replicating the three-dimensional model can then be made using a CAM machine linked to the CAD program. It is also known to the art for the dentist or denturist to use data collected during assessment to create a three-dimensional CAD model of a denture approximating the patient's oral structure, or containing other desired parameters or characteristics. An actual denture replicating the three-dimensional model can then be made using a CAM machine linked to the CAD program. It is also known to the art for the dentist or denturist to fabricate a denture based on information collected during assessment, and then to create a three-dimensional digital model of that actual denture for record purposes, such as through CAD scanning.

It is known to the art to use CAD models, in conjunction with CAM machines, most notably milling machines, to aid in the precise manufacture of custom denture bases, which often include custom-milled sockets for artificial teeth configured to replicate the natural spacing and placement of the patient's teeth. These sockets can then be fitted with selected commercially available artificial teeth, or with custom manufactured artificial teeth. The patient can then undergo an iterative process of test-fitting, providing feedback, and further alteration of the denture base or teeth to achieve proper occlusion and a satisfactory natural fit and feel.

It is known to use plastic as a material for artificial teeth. Plastic artificial teeth are commonly available, relatively inexpensive, and easy to shape and otherwise work with. Plastic teeth can also be easily made to resemble real teeth. Plastic artificial teeth suffer two notable drawbacks. First, plastic artificial teeth are molded, and thus are not consistently sized. Plastic teeth are commonly made from molds with a long service life. Over the course of the mold's service life, material from the wall of the mold wears away, resulting in an increase in the size of the mold cavity. A plastic tooth made from a mold that has been in service for ten years will therefore commonly be larger than a plastic tooth made from that same mold when the mold was new. Additionally, molds contain multiple cavities, and cavity-to-cavity wear is not necessarily uniform. Thus, while a dentist may select artificial teeth of a certain purported size based on the listed size of the mold, the actual size of the tooth may vary from the listed size specifications, even if the same mold is used over time. This variation and uncertainty increases the likelihood that the denture will not be ideally shaped or sized immediately upon adding the artificial teeth, and increases the likelihood that adjustments will be required. Second, plastic teeth wear at significantly quicker rate than natural biological teeth or teeth restored using porcelain or metal materials. Over time, as the plastic teeth wear more rapidly than natural teeth or other tooth surfaces, any natural bite feel accomplished by the original denture can be altered or lost.

It is known to the art to address the problems posed by the inconsistent sizing and rapid wear of plastic artificial teeth by using metal occlusal inserts. These inserts, however, have poor esthetics and ruin the appearance of real teeth that many patients desire from dentures.

The present invention is directed to a method of denture manufacture that incorporates CAM-formed occlusal inserts made of zirconia. Embodiments of the present method are used to manufacture dentures that are more easily shaped and sized to create a natural bite feel, allow the use of plastic artificial teeth, retain the esthetics of natural teeth, and prevent uneven wear between the artificial teeth and the patient's pre-existing natural or restored teeth. Generally, embodiments of the present invention include a method comprising the steps of:

a. Evaluating a patent to determine desired denture parameters;
b. Fabricating a first denture according to those desired denture parameters, the first denture including at least one occlusal portion;
c. Electronically storing the three-dimensional shape and size of the first denture; d. Forming a holding area within at least one of the occlusal portions of the first denture;
e. Preparing a zirconium occlusal insert for attachment to the holding area, where the occlusal insert is sized and shaped to create a denture approximating the desired denture parameters when mated to the first denture; and
f. Attaching said occlusal insert to said holding area to create a useable second denture, where the second denture approximates said desired denture parameters.

BRIEF DESCRIPTION OF THE DRAWINGS

These and other features, aspects, and advantages of the present invention will become better understood with regard to the following description and accompanying drawings, where.

DETAILED DESCRIPTION

The present invention teaches a method of manufacturing dentures using zirconium occlusal inserts, and a denture made by that method of manufacture.

Embodiments of the present invention apply equally to full and partial dentures, and upper and lower dentures. In all embodiments, the method and denture made using the method incorporate occlusal inserts made of zirconia. Zirconia has high thermal resistance, low thermal conductivity, chemical stability, and high fracture strength. It is a high-performance material with excellent biocompatibility and mechanical properties. Zirconia has extreme hardness and wear resistance. Notably, zirconia wears at a rate similar to the wear rate of natural tooth enamel. Zirconia is also colorable and stainable, and can with relative ease be stained to match the esthetics of natural teeth. Zirconia is easily shapeable, and can be readily milled by CAM mills and similar machinery. Zirconia also does not unduly abrade or wear opposing teeth.

The first step in manufacturing a denture (1) according to the teachings of the present method is determining the desired parameters of the denture (1). Parameters include the overall shape and size of the denture (1) and the shape, size, and relative location and orientation of each denture component, including the base, the teeth, and any occlusal inserts (5). Preferably, the desired parameters are all of those parameters that relate to obtaining the desired fit and feel when the denture is used by the patient, preferably a natural bite feel.

The determination of desired parameters is preferably reached through evaluation of the patient by a dentist. This is particularly the case when the desired parameters are those that will result in a natural bite feel. Methods of evaluation the patient to determine the desired parameters are well known to the art, and result in the generation of a substantial amount of information about the patient's landmark oral structures, resting jaw position, muscle, jaw, and tooth movement during normal mastication and speech, the spacing and orientation of teeth, and general bite registry and occlusion characteristics. Approximating these parameters when a denture is in use is, as known to those skilled in the art, essential to preserving the preferred and desired natural bite feel.

As known to the art, the dentist may use a haptic bite pad or other electronic device to obtain computer assistance in calculating the desired parameters and modeling the desired denture, from which a physical denture may be made using known techniques such as CAD/CAM or 3D printing. Alternatively, a dentist may evaluate the patient using manual or other known methods, may determine desired parameters based on that evaluation with or without computer assistance, and may input selected data or parameters into a CAD or similar computer modeling program to generate a three-dimensional model of the desired parameter denture, from which a physical denture may be made using known techniques such as CAD/CAM or 3D printing. Preferably, the dentist evaluates the patient using known methods, determines desired parameters based on that evaluation with or without computer assistance, and those parameters are used to by the dentist or a denturist to create a physical denture. This physical denture, whether created in the preferred manner or by some other method, will be referred to as a "first denture."

After evaluation of the patient and determination of the desired denture parameters, the next step herein is to fabricate a first denture. A first denture according to the teachings of this invention comprises a base portion with a first side configured to overfit at least a portion of the patient's gums and a second side comprising one or more sockets configured to contain artificial teeth. This base portion is typically made of acrylic. The base portion can be purchased commercially and optionally modified, or, preferably, can be made from stock materials by known methods, such as by CAD/CAM, 3D printing, or by hand, to match as closely as possible the desired parameters. A "first denture" as used herein may refer to an upper partial, a lower partial, an upper full, a lower full, or any upper and lower set.

The step of fabrication of the first denture further includes selecting and inserting artificial teeth into the sockets. These artificial teeth can be custom fabricated or molded to approximate or match the desired parameters, or can be purchased commercially in pre-determined or custom shapes, sizes, or configurations. In preferred embodiments hereof, such artificial teeth are made of plastic, most preferably polymethylmethacrylate plastics. Because the occlusal fit of the finished denture of the present invention will be determined by a separate occlusal insert, the artificial teeth in dentures of the present invention do not need to be selected to result in a first denture precisely matching all of the desired parameters, particularly occlusal parameters. The artificial teeth may be removably attached to the denture base during this step, or may optionally be permanently attached to the denture base during this step. Preferably, permanent attachment of artificial teeth to the denture base is accomplished by adhesive bonding, as would be appreciated by one skilled in the art.

Figure 1:
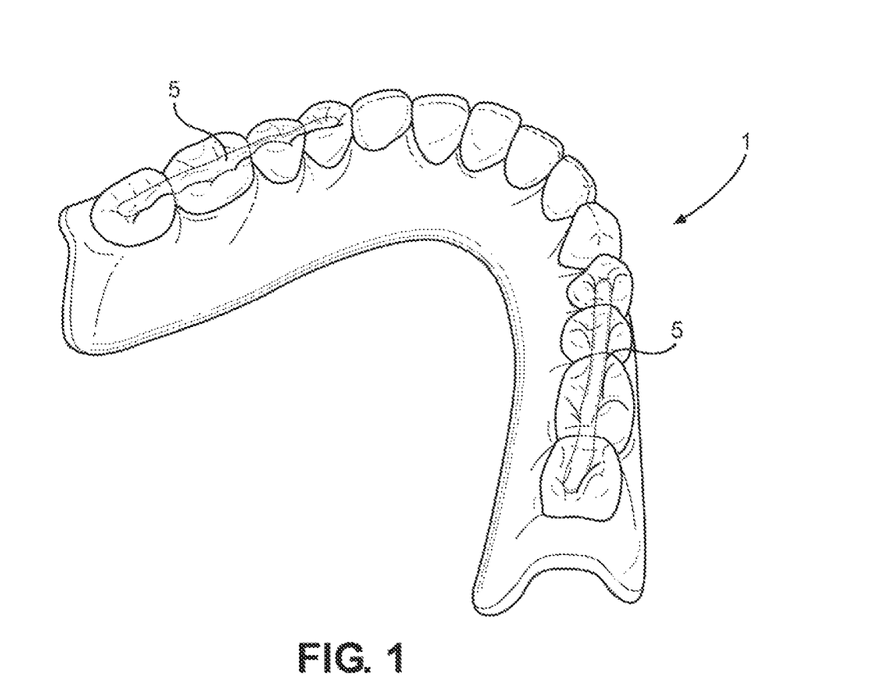
FIG. 1 shows a perspective view of a lower full denture according to the teachings of the present invention.
Figure 2:
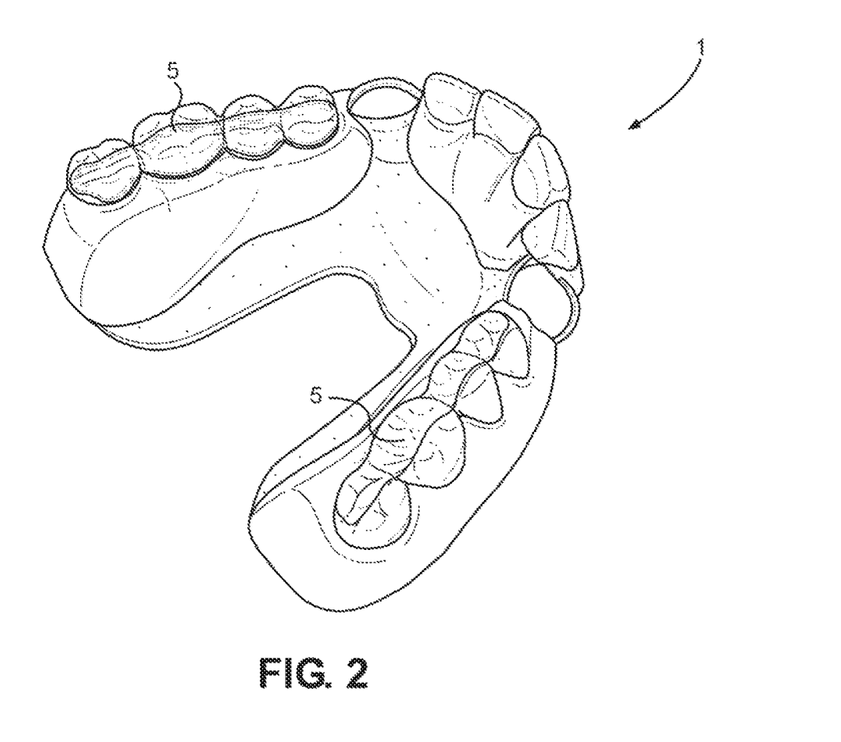
FIG. 2 shows a perspective view of a partial lower denture according to the teachings of the present invention.
Figure 3:
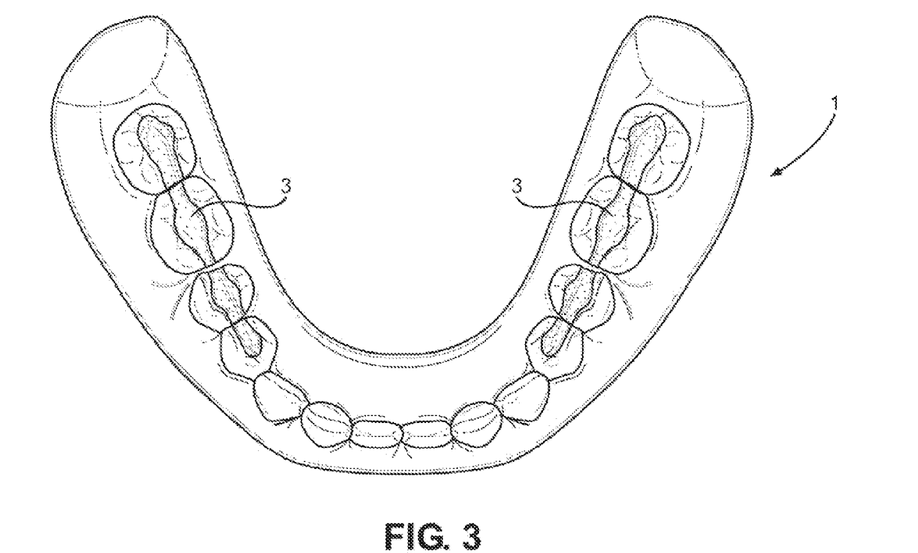
FIG. 3 shows a top-down view of a full lower denture according to the teachings of the present invention after the step of forming holding areas within the denture and prior to the step of attaching an occlusal insert.
Figure 4:
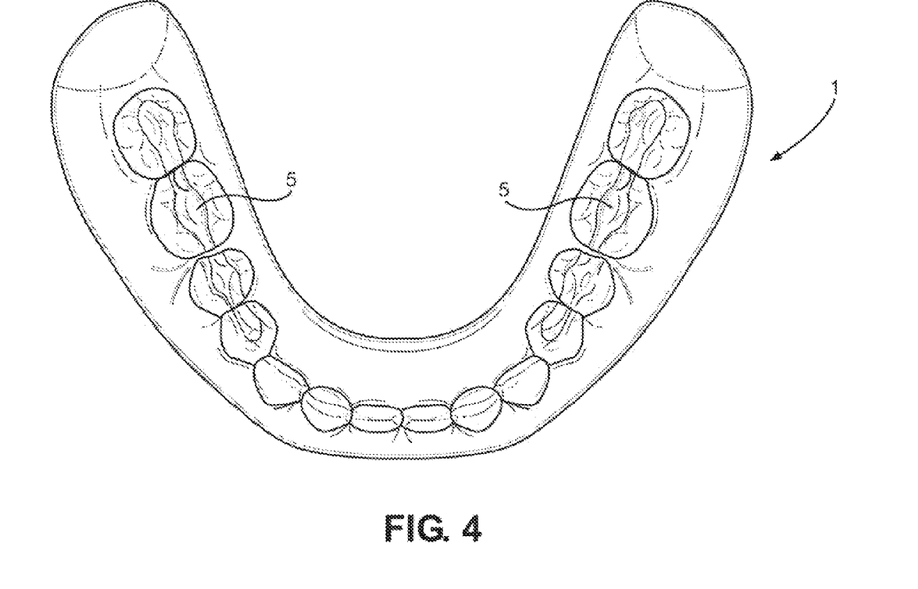
FIG. 4 shows a top-down view of a full lower denture according to the teachings of the present invention after the step of attaching an occlusal insert.
Figure 5A:
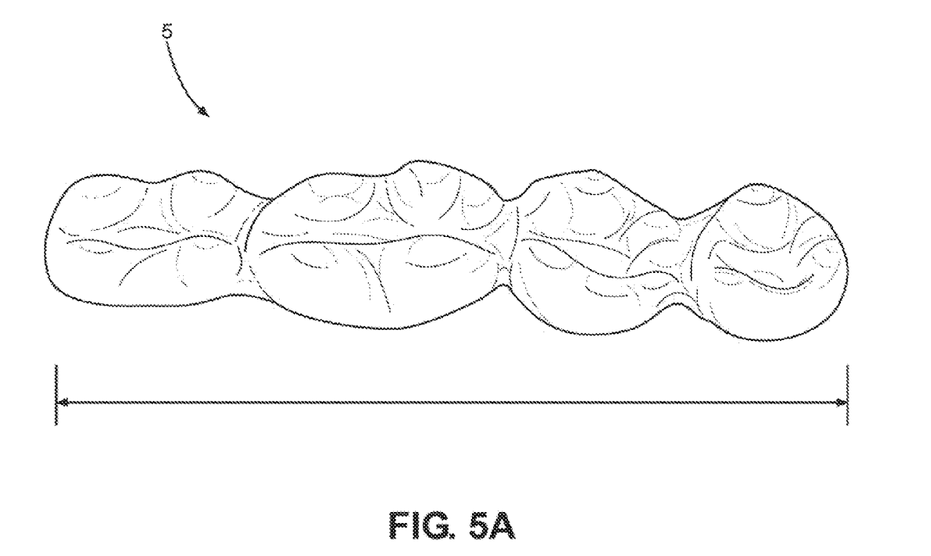
FIG. 5A shows a perspective view of an occlusal insert for a lower denture manufactured according to the teachings of this invention prior to the substep of reducing the size by sintering.
Figure 5B:
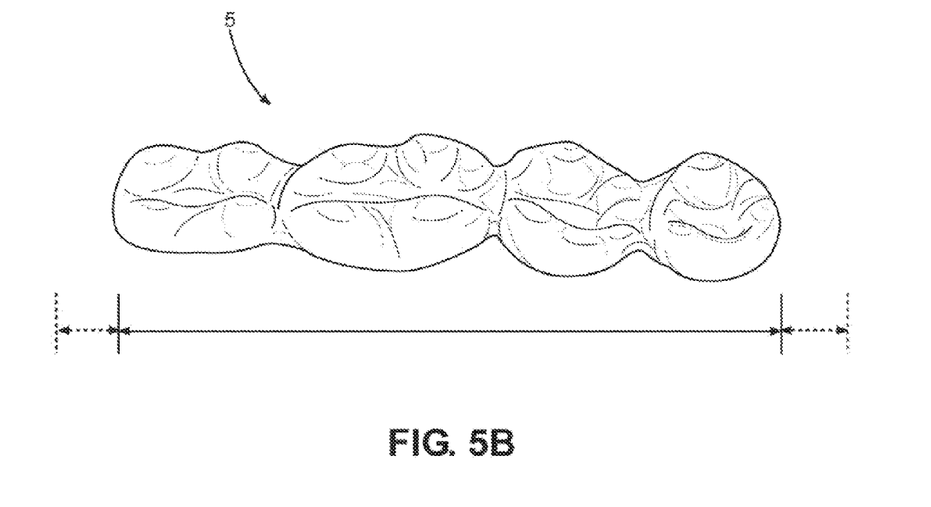
FIG. 5B shows a perspective view of an occlusal insert for a lower denture manufactured according to the teachings of this invention alter the substep of reducing the size by sintering.
Figure 6:
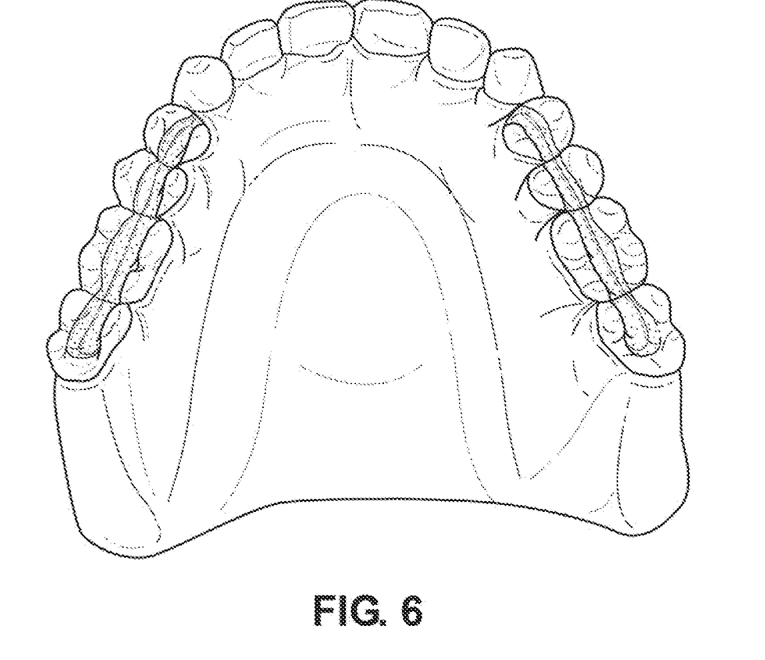
FIG. 6 shows a perspective view of a full upper denture according to the teachings of the present invention after the step of forming holding areas within the denture and prior to the step of attaching an occlusal insert.
Figure 7:
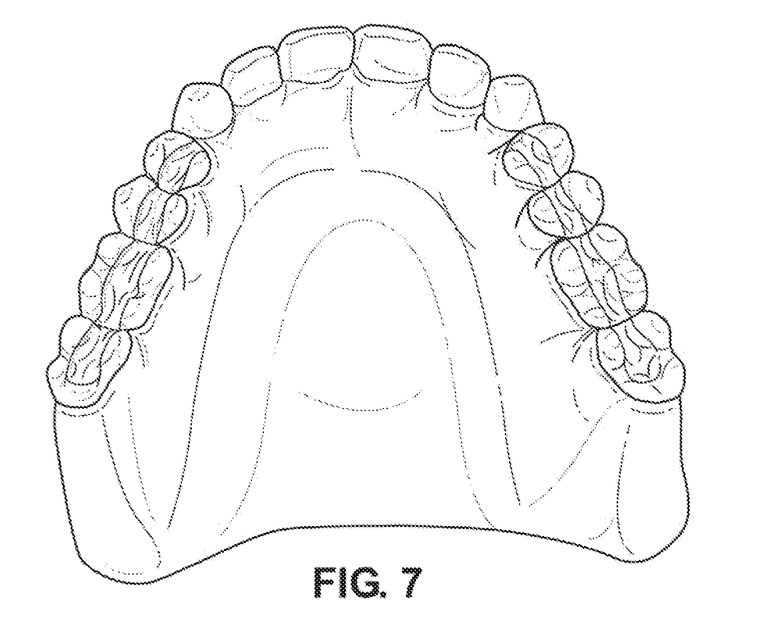
FIG. 7 shows a perspective view of a full upper denture according to the teachings of the present invention after the step of attaching an occlusal insert.
Figure 8:
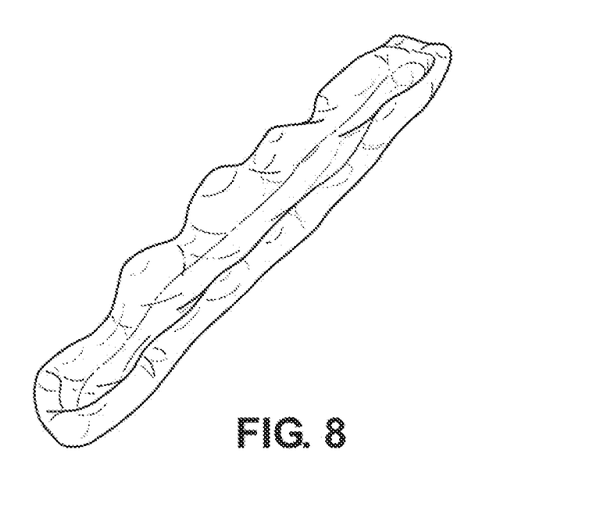
FIG. 8 shows a perspective view of an occlusal insert for an upper denture manufactured according to the teachings of this invention.

The first denture comprises at least one occlusal portion. The occlusal portion, as that term is used herein, refers to that portion or portions of the surface of the artificial teeth attached to the denture base anticipated to function as an occlusal surface when the patient uses the denture. The location of the occlusal surface or surfaces will, as would be appreciated, vary on a patient by patient basis depending on the particular characteristics of that patient's oral structures, jaw, jaw musculature, and teeth. Also, depending on whether the denture is upper or lower, and whether it is full or partial, and whether its artificial teeth oppose gums, oppose natural teeth, or oppose the artificial teeth of another denture, the denture may have one occlusal portion, or may have more than one occlusal portion. The Figures above, and particularly FIGS. 3 and 6, show common locations for occlusal portions.

After fabrication of the first denture, its three-dimensional size and shape is determined and stored electronically, preferably by use of a CAD scanner in conjunction with a CAD software program. Alternatively, the size and shape of the first denture may be manually inputted into a CAD program or drawn using CAD based on manually determined measurements.

The first denture is then prepared for occlusal inserts (5) by forming one or more holding areas (3) within the first denture. These holding areas (3), as can be seen in FIGS. 3 and 6, comprise voids or other apertures, and preferably slots, formed into the occlusal portions of the artificial teeth. These holding areas (3) are configured to retain custom-made occlusal inserts (5). These occlusal inserts (5) will ultimately be inserted within the holding areas (3) and permanently bonded there. Holding areas (3) may be formed by a variety of mechanical processes. Holding areas (3) may be cut, milled, drilled, or sanded into the occlusal portions. The location, size, and depth of each holding area (3) may be determined manually, and the holding area may be formed manually. Preferably, however, the holding areas (3) are milled at a desired location, in a desired shape, to a desired depth, using a CAM mill. As would be appreciated by one skilled in the art, one, two, three, four or more holding areas may be desired to be formed into a first denture. Further, a single holding area may be formed across multiple occlusal surfaces. In that case, the holding area may be formed into both occlusal and non-occlusal surfaces. Preferably, after the holding area or areas are formed, the first denture is placed in a CAD scanner once again and a new three-dimensional model is made. In the preferred embodiment hereof, this second three-dimensional model can be compared to the first three-dimensional model to determine the shape and size of occlusal insert needed for insertion into the holding areas to bring the denture back to the natural fit configuration, and to otherwise ensure that alignment and orientation of the first denture has not been inadvertently or undesirably altered by the formation of holding areas. If such alteration has occurred, comparison of the first and second three-dimensional models can be used to determine what adjustments should be made to bring the first denture back to the desired alignment and orientation.

The first denture must represent, as closely as possible, an ideal occlusal relationship prior to the step of forming holding areas. As would be appreciated by one skilled in the art, failure of the first denture to represent an ideal occlusal relationship dramatically increases the odds that the second denture provided to the patient will not have a satisfactory fit and feel.

For each holding area formed in the first denture, a custom sized and custom shaped zirconium occlusal insert (5) is prepared. Preparation of the occlusal insert (5) includes selecting zirconium stock based on desired color and esthetic characteristics and forming the occlusal insert to a desired shape and size. The initial size and shape of the occlusal insert (5) is selected so that when the occlusal insert or inserts (5) are completely prepared and fitted within the holding area or areas, the result is a denture (1) with an overall shape, size, and parameters that approximate the desired parameters, and preferably that replicate closely the shape, size, and parameters of the first denture prior to the step of forming holding areas.

Preferably, the occlusal insert (5) is formed by CAM milling from zirconium stock. Most preferably, the occlusal insert (5) is created by a CAM mill guided by the CAD electronic three dimensional model of the first denture such that the occlusal insert (5) is shaped on its non-occlusal side for insertion into the holding area and shaped on its occlusal side to form tooth surfaces with the desired parameters. Preferably, the CAM mill is directed to form an occlusal insert (5) with the occlusal shape and profile shown by the electronically stored three dimensional image of the first denture, along with a non-occlusal profile configured to fit within the holding area, but oversized to account for shrinkage of the zirconia during the preferred sintering step. Preferably, the occlusal insert (5) is formed approximately 15% to approximately 20% oversized, with the precise degree of oversizing contingent on the specific sintering conditions intended to be used. Most preferably, the occlusal insert is formed approximately 17.8% oversized. A separate occlusal insert (5) is created for each holding area (3).

Preferably, the step of preparing the occlusal insert (5) includes sintering the occlusal insert (5) after forming it. Sintering improves the properties of zirconia for use as an implant, and particularly improves flexural strength, as would be appreciated by one skilled in the art. Sintering for zirconia used in implants is typically performed at temperatures between 1,300 degrees Celsius and 1,700 degrees Celsius, with the greatest improvement in flexural strength occurring at around 1,500 degree Celsius. In preferred embodiments of the present invention, sintering is performed at temperatures of approximately 1,500 degrees Celsius. Time of sintering is dependent on volume, temperature, and method. Although microwave sintering, conventional sintering, and other sintering methods may be used, the occlusal insert of the present invention is preferably sintered using conventional sintering for between approximately 8 and approximately 12 hours, and most preferably for approximately 10 hours.

Optionally, the step of preparing the occlusal insert (5) may include staining the occlusal insert to a desired shade, color, or tone, such as to match or simulate real teeth. Such staining, as would be appreciated by one skilled in the art, may occur at virtually any stage of the method. Preferably, staining occurs during sintering.

After the occlusal insert (5) is prepared, it is attached to the first denture by inserting the non-occlusal surface of the insert into the correspondingly shaped holding area (3) to form a denture that closely approximates the first denture, which in turn closely approximates the desired natural bite parameters The denture formed by insertion of the occlusal insert (5) into the corresponding holding areas (3) of the prepared first denture is referred to herein as a "second denture." It should be noted that the second denture is not a separate structure from the first denture; rather it is the revision of the first denture created by the formation of the holding areas and the removable or permanent attachment of the prepared occlusal inserts to those holding areas. If the occlusal insert (5) does not obtain the desired fit within its corresponding holding area (3), or if insertion of the occlusal insert or inserts (5) does not otherwise result in a second denture that adequately approximates the desired parameters, one or more of the occlusal inserts may be removed and may undergo further preparation. Such further preparation may include, by way of example, additional sintering, milling, sanding, abrading, cutting, or other shaping.

After the occlusal insert or occlusal inserts are determined to be suitably prepared, the occlusal insert or occlusal inserts may be permanently attached to the holding areas (3). Preferably, however, the prepared occlusal insert or inserts are first removably inserted into the holding areas for test-fitting with the patient. During test-fitting, the dentist may assess whether the second denture creates the desired fit and feel for the patient, preferably a natural bite feel. The dentist may assess the patient objectively, including recording occlusal patterns or data. The dentist may separately or additionally solicit or accept subjective feedback from the patient concerning the fit and feel of the second denture. Based on this further assessment, the second denture may be further shaped or altered responsively to the assessment, including the patient's preferences and the dentist's judgment of the patient's needs. This test-fitting and revision process may, as would be appreciated, be repeated until the second denture creates a fit and feel satisfactory to the patient and the dentist. This further test-fitting and further evaluation step may optionally and preferably be completed after the occlusal formation substep, but before the sintering substep.

After the second denture is determined to be satisfactory to the patient and the Dentist—which preferably but optionally includes the further assessment discussed above—the second denture is finished. The occlusal insert or inserts are stained, if staining is desired and has not yet been performed, are sintered, if sintering is desired and has not yet been performed, and are permanently attached to the holding area or areas, if permanent attachment has not yet been achieved. Such permanent attachment can be accomplished through the use of adhesives or resins, using techniques known to the art. Preferably, permanent attachment is accomplished by cleaning the occlusal insert or inserts and holding area or areas with a solvent such as alcohol, applying a first primer to the surface of the occlusal insert that will contact the surface of the holding area, applying a second primer to the area of the surface of the holding area that will contact the surface of the occlusal insert, applying a bonding agent such as a dual-cure resin cement to both surfaces, attaching the occlusal insert to the holding area in the desired orientation, extravagating excess bonding agent, and allowing the bonding agent to finish curing. A wide variety of adhesives and adhesive attachment techniques may be used within the scope and spirit of this invention.

Although the present invention has been described in considerable detail with reference to certain preferred versions thereof, other versions are possible. For example, materials, shapes, sized, or configurations other than those described in detail herein may be used for the versions of this invention. Further, the method may include additional steps, intervening steps, or steps performed in an order other than those specified in the embodiments described above. Therefore, the spirit and scope of the claims should not be limited to the description of the preferred embodiments described herein.

What is claimed is:

1. A method for making dentures, said method comprising the steps of:
    a. Evaluating a patent to determine desired denture parameters;
    b. Fabricating a first denture according to said desired denture parameters, wherein said first denture comprises at least one occlusal portion;
    c. Electronically storing the three-dimensional shape and size of said first denture;
    d. Forming a holding area within at least one of said occlusal portions;
    e. Preparing a zirconium occlusal insert for attachment to said holding area, wherein said occlusal insert is sized and shaped to create a denture approximating said desired denture parameters when mated to said holding area; and
    f. Mating said occlusal insert to said holding area to create a second denture, wherein said second denture approximates said desired denture parameters.

2. The method of claim 1, further comprising the steps of:
    a. Test fitting said second denture to the patient;
    b. Assessing the patient; and
    c. Shaping at least one of said teeth, said occlusal insert, or both, responsively to said assessment.

3. The method of claim 2, further comprising the step of permanently attaching said occlusal insert to said holding area.

4. The method of claim 3, wherein said step of forming a holding area to receive an occlusal insert comprises at least one of milling, cutting, and forming one holding area within one occlusal portion.

5. The method of claim 3, wherein said step of forming a holding area to receive an occlusal insert comprises at least one of milling, cutting, and forming one holding area within each of two separate occlusal portions.

6. The method of claim 3, wherein said step of forming a holding area to receive an occlusal insert comprises at least one of milling, cutting, and forming one holding area within each of three separate occlusal portions.

7. The method of claim 3, wherein said step of forming a holding area to receive an occlusal insert comprises at least one of milling, cutting, and forming one holding area within each of four separate occlusal portions.

8. The method of claim 3, wherein said step of electronically storing the three-dimensional shape and size of said first denture comprises storing the three-dimensional shape and size of said first denture in a CAD program.

9. The method of claim 8, wherein at least one of the step of fabricating a first denture and the step of forming a holding area is performed by a CAM mill.

10. The method of claim 9, wherein the step of preparing a zirconia occlusal insert comprises the substeps of:
   a. Forming said occlusal insert to a first shape and a first size; and
   b. Sintering said occlusal insert to a first shape and a second size, wherein said first shape and second size are selected to create a second denture approximating said desired denture parameters.

11. The method of claim 10, wherein the substep of forming said occlusal insert to a first shape and a first size is performed by a CAM mill.

12. The method of claim 11, wherein said first shape and first size are determined using the electronically stored three-dimensional shape and size of said first denture.

13. The method of claim 12, wherein the substep of sintering further comprises sintering said occlusal insert at approximately 1500 degrees Celsius.

14. The method of claim 13, wherein the substep of sintering further comprises sintering said occlusal insert for between approximately 8 and approximately 12 hours.

15. The method of claim 14, wherein the substep of sintering further comprises sintering said occlusal insert for approximately 10 hours.

16. The method of claim 15, wherein said first size is approximately 15% to approximately 20% larger than said second size.

17. The method of claim 16, wherein said first size is approximately 17.8% larger than said second size.

18. A custom denture with occlusal inserts, said denture comprising:
   a base portion configured to overfit at least a portion of a patient's gums, said base portion comprising one or more sockets;
   plastic artificial teeth attached to said sockets, said teeth comprising at least one occlusal portion and each said occlusal portion comprising a holding area; and
   a zirconium occlusal insert attached to each holding area;
   wherein said custom denture has desired parameters.

19. The custom denture of claim 18, wherein said denture is a full denture.

20. The custom denture of claim 19, wherein said denture is a partial denture.

* * * * *